United States Patent [19]

Halek et al.

[11] 4,007,420
[45] Feb. 8, 1977

[54] DEVICE FOR MEASURING A NOCICEPTIVE REACTION OF LABORATORY ANIMALS

[75] Inventors: Jan Halek; Jaroslav Jezdinsky, both of Olomouc, Czechoslovakia

[73] Assignee: Rektorat University Palackeho v Olomouci, Olomouc, Czechoslovakia

[22] Filed: May 8, 1975

[21] Appl. No.: 575,502

[52] U.S. Cl. .............................. 324/181; 324/65 P; 324/28 R
[51] Int. Cl.[2] ........................................... G04F 8/00
[58] Field of Search ........................ 128/420–422, 128/DIG. 7; 324/181, 28, 62, 65 P, 65 R

[56] References Cited
UNITED STATES PATENTS

3,139,085  6/1964  Custance ..................... 324/65 P

Primary Examiner—Palmer C. Demeo
Assistant Examiner—Michael J. Tokar

[57] ABSTRACT

Apparatus is described for effecting an objective measurement of the intensity of pain induced by a nociceptive irritation of one of the paws of a laboratory animal. The degree of pain is manifested by the animal's repetitively lifting the injured (i.e., test) paw. The test paw is normally in contact with a pair of adjacent conductors of a planar conductor array forming the floor of the animal's cage. Such paw is provided with an electroconductive coating on its plantar surface, so that when such paw is irritated each resultant lifting of the paw from the surface breaks the contact between the bus bars. The total time over which the conductively adapted test paw completes the circuit between the bus bars during a prescribed measurement interval is recorded, together with the total number of disconnections of the paw-base contact over such interval.

4 Claims, 8 Drawing Figures

DEVICE FOR MEASURING A NOCICEPTIVE REACTION OF LABORATORY ANIMALS

The invention relates to a device for measuring a nociceptive reaction of laboratory animals wherein the reaction is manifested by an animal's lifting a paw from a cage floor or other base and holding it above the base for a duration determined by the nature of the nociceptive stimulus.

Such devices are very important in practice, because they are applied in pharmacology for discovering new medicaments that keep down pain. Many devices for evaluating pain in laboratory animals have been designed in the past, but their results are not satisfactory. The main disadvantage of those devices is that they are designed on the principle of defensive spinal cord reflexes (Charpentier - 1964) without the possibility of an objective evaluation and quantitative expression of the intensity of the reaction. Other methods evaluate different kinds of reaction to pain with respect to a psychological component, but they are so complicated and they take so much time that they cannot be employed for everyday work; they also do not have the capability of producing a really objective measurement of reactions (Charpentier - 1961, Evans - 1961, Römer - 1968, Weiss and Laties - 1961, Weitzman and Ross - 1962 etc.).

Devices are known which work on the principle of a thermal irritation, when experimental animals (mice, rats) are exposed to a thermal affecting e.g. a tail tip of an animal placed in a fixing cage, or the skin of an animal, and an interval is measured (time of latention) when a reflex swerving movement is performed (D' Amour and Smith - 1941, Arcoli and Lewis - 1945, Pfeiffer and coll. - 1972). There is another variant of such devices, viz. to put mice in a tank the bottom of which is heated to a higher temperature, approx. 55° C. In this case, one finds out an analgesic effect of a medicament with respect to a prolonged interval when mice start licking paws, or when they try to escape by a jump (Eddy and Leimbach - 1953). All these cases concern devices by which an effect of weak analgesics, type acetylosalicylicacid, and analgesics of the group of morphine antagonists (Grossman and coll. - 1960, Wilhelmi and coll. - 1968, Archer and coll. - 1972) cannot be demonstrated.

Devices are also known that cause pain by mechanical pressure, e.g. when a so-called arterial clamp is fixed onto a mouse tail (Haffner - 1929, Herz - 1962, Metys and coll. - 1971) or by an increasing pressure of a piston onto a tail or paw of a rat (Green and coll. - 1951, Collier and coll. - 1956, Winder and coll. - 1966). An analgesic effect is evaluated in this case according to a prolonged interval up to a pain reaction (a cry, a bite, an escape) at a constant pressure or at an increasing pressure e.g. to a double value till a pain reaction takes place. It is also impossible to prove the effect of weak analgesics by means of these devices (Grossman and coll. 1960), or the results are not specific ones, i.e. they prove an analgesic effect of drugs which do not keep down a pain feeling in clinical practice (Wilhelmi and coll. - 1968).

An electric current has also been applied to produce pain. One irritates a tooth pulp of dogs (Koll and Reifert - 1938), rabbits (Yim and coll. - 1955) or guinea pigs, or different parts of a surface of animal bodies. Electrodes are placed mostly onto a tail of a rat (Caroll and Lim - 1960, Charpentier - 1962, 1964, 1972), or onto a tail of other animals, e.g. monkeys (Römer - 1968). In other devices, rats are placed in a box with a floor made of steel wires, and electric current irritates paws of the animals in the box (Ewans - 1961, Houser and Paré - 1972, 1973a, 1973b). A pain reaction is here evaluated with respect to a minimum strength of electric current that causes a pain irritation (threshold of pain), or according to a complex reaction to a pain at a stronger over-treshold irritation. All these kinds of evaluation are very tiresome and they take much time; usually they are not specific ones and it is difficult to apply them in everyday practice.

Psycho-pharmacological tests are known which apply an irritation by means of electric current having an increasing irritation either on rat body surface (Weiss and Laties - 1961) or directly on brain structures by means of stereotactically implanted electrodes e.g. if it concerns monkeys (Boren and Malis - 1961, Weitzman and Ross - 1962). Animals are trained in advance for a long time that they may stop an irritation by pressing down a push-button when feeling a pain. In this case, attention is paid to the strength of the current when the animal stops the irritation. These methods are so sensitive that they may prove an analgesic effect of week analgesic, but they are so tiresome and they take so much time that they usually have place only in a theoretical research.

Methods are known of applying chemical substances to induce pain, i.e. different irritants or so-called mediators of pain (bradykinin, serotonin, histamine, acetylcholin) that are injected into animals either intraperitoneally or intra-arterially. One applies mostly the method according to Siegmund et al (1957) or different modifications of it, when a solution of phenylchinon or a solution of acetic acid is injected intraperitoneally into mice, or to rats (Whittle - 1964, Metys or also coll. - 1971), and bradykinin and acetylcholine may be used for this purpose (Collier et al - 1964). These substances having been applied, animal twist and strain the whole bodies, whereby their abdomen walls contract. This test is called internationally the "writhing test," or a test of peritoneal irritation.

After having injected such an irritant, the animals are being observed - the analgetic effect of a drug being expressed by its dose - which prevents the appearance of typical reactions in 50 per cent of the test animals. This test is very sensitive, as it proves an effect of strong and weak analgesics and even of analgesics of the group morphine antagonists (Archer and coll. - 1972, Pearle and Harris - 1966), but it is not a very specific one. One gets many falsely positive results, when e.g. chlorpromazin and other analgesically ineffective neuroleptics are very effective in this test (Metys and coll. - 1971, Houser and Pare - 1973b). Another variant of these chemical tests is an intraarterial injection of bradykin by means of a catheter which is introduced surgically into a spleen artery of dogs and cats (Guzman et al - 1964, Lim and Guzman - 1968) or into a carotid artery of rats (Blane 1967). During these tests bradykin is injected into an artery, and the appearance of a brief reaction to pain is observed (twisting or crying of animals). The criterion of an analgetic effect of the drug tested is its capability to prevent the appearance of this reaction to bradykinin in 50% of the test animals. This test seems to be sufficiently sensitive and specific, but it does not make possible the evaluation of the intensity of pain, and moreover, it takes much time, so that it cannot be applied to a great number of animals. To investigate an analgesic effect of medicaments one may use an indirect criterion, i.e. the minimizing of a hyperalgesis in response to a mechanical stimulation excited by an inflammation (Lim and Guzman - 1968). La Belle and Tislow (1950) and Margolin (1965) apply to rats, to excite the inflammation an intraarticular injection of silver nitrate solution into an ankle-joint, which is excited by a forced movement of the limb in question. An analgesic effect is evaluated by suppressing the appearance of this reaction in 50% of the test animals.

In recent years there has often been used a method according to Randall and Selitto (1957) in the pharmaceutical industry, wherein the analgetic effectiveness of so-called non-steroidal antiflogistics (indomethacin, phenylbutazone etc.) is evaluated according to the decrease of hyperalgesia excited by an inflammation of a rat paw. The inflammation is caused in this case by a subplantar injection of brewers yeast suspension or of a carrageenin solution (Silvestrini and coll. - 1966); the pain reaction is evaluated according to the piston pressure in mms of mercury column when a defensive reaction of the animal appears. This method, as to its pain reaction, is near to the desired kind of pathological pain, but it has several important disadvantages. First it is a non-physiological position of the animal that must be held with force when carrying out the measurement (additional sensory percepts affect the perception of pain feeling very much - Keidel - 1972); a subjective kind of evaluation of the reaction to pain is another disadvantage. It causes a variability of results; that is the reason why measurements of large groups of animals must be performed. Data of a spontaneous pain feeling during an inflammation cannot be received in this case. One also knows an evaluation of an analgesic effect of medicaments according to keeping down the function affected by an inflammation, when a reaction to inflammatory pain is excited by injecting a solution of formalin into an ankle of a hind limb of a dog and one watches when movements in the respective ankle of these dogs cease at a forced walk (Pardo and Rodriguez - 1966, 1968). A special scanner fixed to the ankle, the pulses of which are registered on a polygraph, enables the evaluation to be made.

This evaluation is rather sensitive in proving an analgesic effect of weak analgesics, but it is expensive if it concerns devices, instruments and experimental animals (5 -30 dogs is one group for one dose of a substance; the price of dogs is high and there are difficulties with their keeping); so it is not possible to apply it for everyday work. A quantitative evaluation of the record is tiresome and it is not very precise. It was found out that dogs give relief to the respective limb after an intraarticular injection of Na-urate suspension. To get an objective measurement of this phenomenon, dogs are put on a system of four scales each supporting a leg and changes in the loading of each scale are noted (Fujihira and coll. - 1971). The reaction to pain causes a decrease of the weight being supported with the affected leg and an increased loading of the one on the other side; non-steroidal antiflogistics (acetylocalicylic acid etc.) keep down these changes in such loading unbalance due to the suppression of inflammatory pain. This method demonstrates in an objective manner a feeling of a spontaneous pathological pain, excited by an inflammation, and it is the best of all other methods as to the requirements for an evaluation of an analgesic effect of weak analgesics. A disadvantage of it is that it requires much time and experimental animals as well. That is why even this method is not suitable for an everyday practice on a large scale.

Some of the above-mentioned disadvantages are obviated by a device for measuring nociceptive reactions of laboratory animals according to the present invention. The apparatus of the invention is based on the observation that the nociceptive stimulation of one paw of a laboratory animal such as a rat, guinea pig or the like causes a typical paw-lifting response, which is a withdrawal reflex reaction to the painful injury of the test paw. During such reaction, the animal holds the lifted injured paw above the floor of the cage where the animal is situated, standing in the meanwhile on its three uninjured paws which are continually in touch with the base. Moreover, the animal typically intermittently contacts the base with its injured paw, lifting it up again immediately because such a contact intensifies the pain sensation. This kind of nociceptive stimulation may be induced in laboratory animals in various ways, e.g., by injecting solutions of pain mediators (such as bradykinin) or of other irritants (such as formalin, yeast suspension, or the like) into the paw, or by physically injuring the paw.

The apparatus of the invention is adapted to measure, during a prescribed measurement interval, the total time over which a conductively adapted plantar surface of a test paw of the animal contacts the floor of the cage in which the animal is placed. The apparatus is also adapted to measure the total number of disconnections of the paw-base contact.

The paw to be conductively adapted is treated to effect a good electrical contact with a planar array of conductors that forms substantially the entire floor of the animal's cage. Such contact is facilitated by providing, on the plantar surface of the test paw, an adhesive layer of a suitable electroconductive varnish. Such substance greatly increases the electroconductivity of the test paw relative to the conductivity of the other three paws, even if such other paws are wet.

The making and breaking of the test paw-base contact is adapted to selectively change the conductive state of a twostate comparator, which in turn controls the recording of the total paw-base contact time and the number of paw-base disconnections during a measurement interval. Such total contact time is employed as a principal criterion of the nociceptive reaction, i.e., of the paw-lifting behavior. In particular, decreases in the contact time have been found to be proportional to increases in intensity of the nociceptive reaction, while the number of paw-base disconnections during such measurement interval has been found to be directly proportional to the nociceptive stimulus. Such reaction of the animal may be substantially decreased, or even suppressed completely, by drugs which are active in suppressing the feeling of pain but not the consciousness of the animal.

The device according to the invention will be now described by way of example with reference to the accompanying drawings, in which:

FIG. 8 is a detail wiring diagram of one channel of the second embodiment of the invention for the continuous recording of time.

Figure 1:
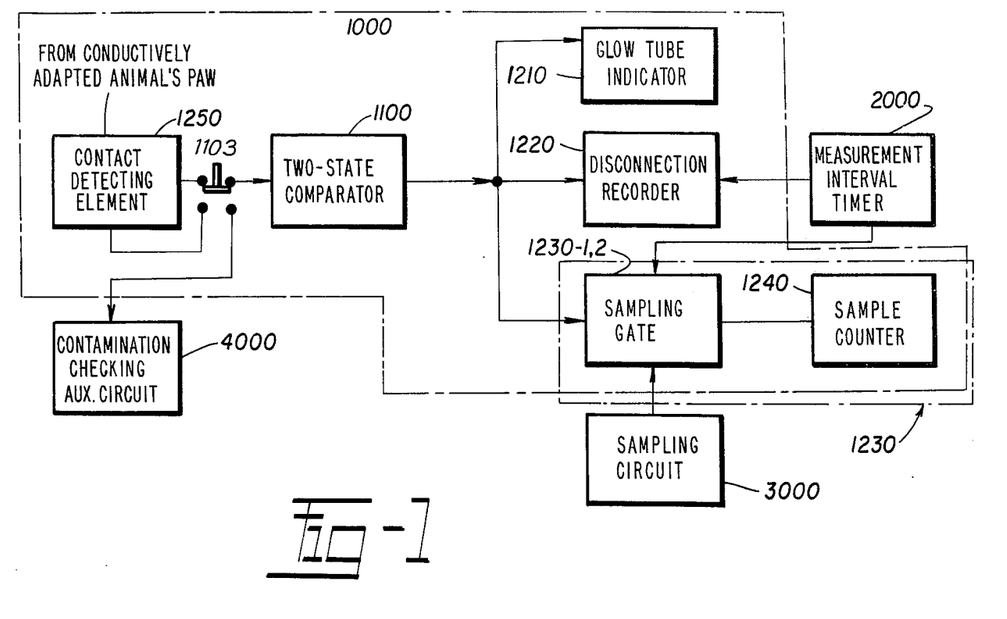
FIG. 1 is a block diagram of one channel of the first described embodiment of the device of the invention provided with means for discretely recording the total time, during a measurement interval, in which a conductively adapted paw of a test animal is in contact with an electroconductive base of the animal's cage.
Figure 7:
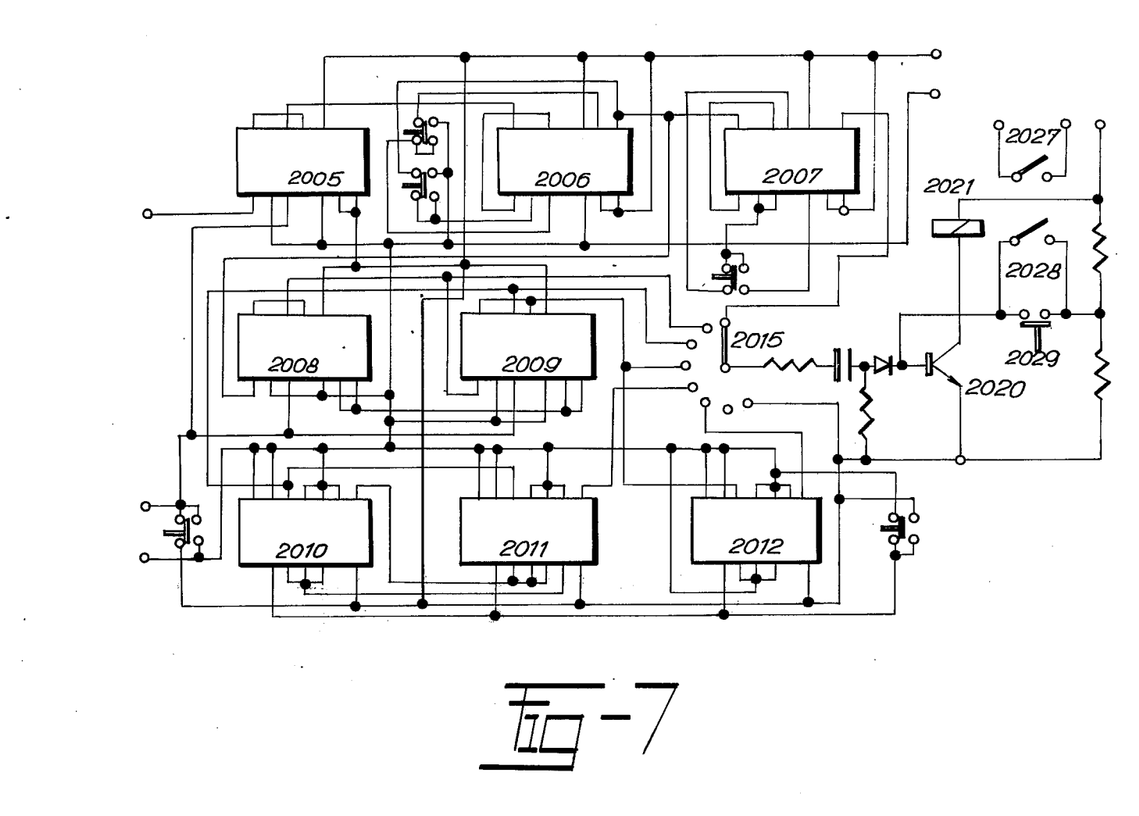
FIG. 7 is a wiring diagram of a timer which may be advantageously employed to select the measurement time interval in the device of the invention.
Figure 9:
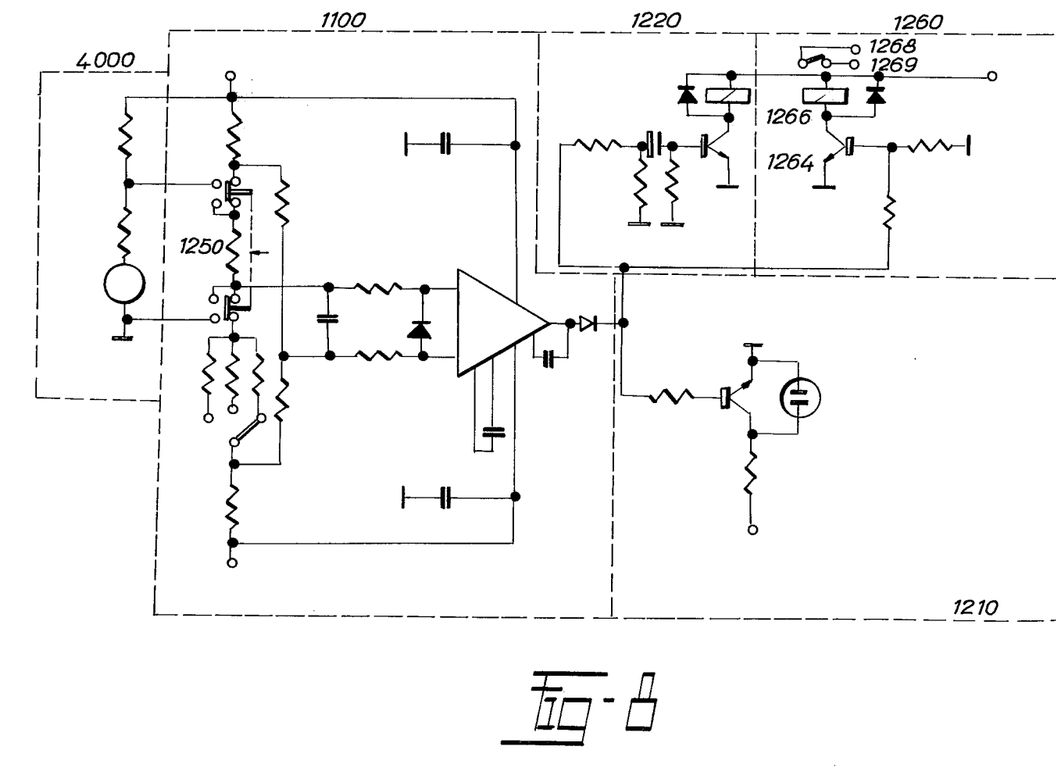

In FIG. 1 there is shown a first illustrative embodiment of one channel 1100 of the device of the invention for measuring a nociceptive reaction of laboratory animals, such device being provided with means for the discrete recording of the time, during a selected measurement interval determined by a timer of FIG. 7, over which an electroconductively adapted plantar surface of a test paw of a laboratory animal (not shown) is in contact with a detecting element 1250 described below.

Figure 3:
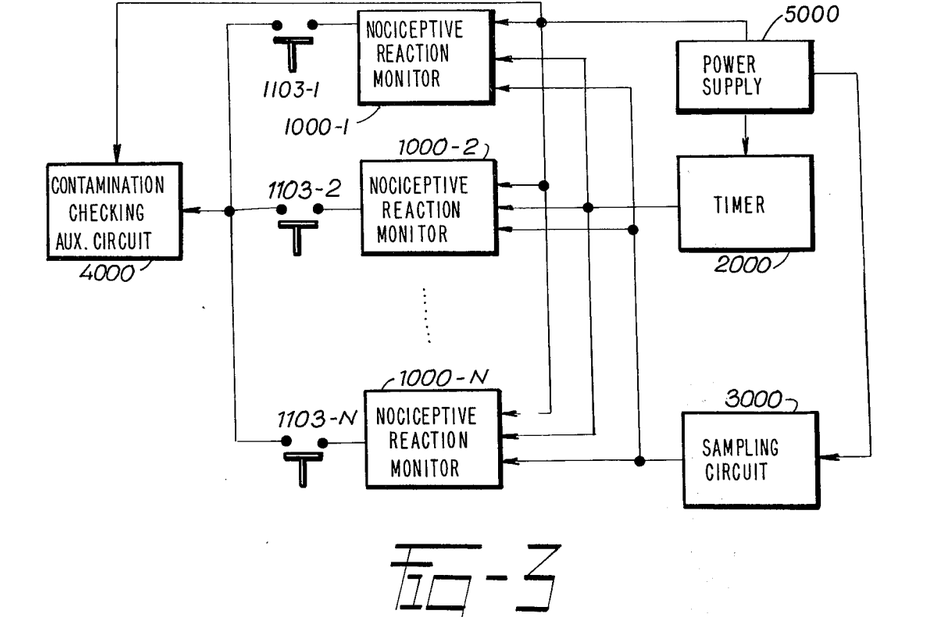
FIG. 3 is a general block diagram of the device of the invention.

The device shown in FIG. 1 further includes a comparator 1100 in the form of an operational amplifier, a glow tube indicator 1210, a circuits 1230, 1240 for recording the time during which the conductively adapted paw is in contact with the element 1250, and a circuit 1220 for recording the total number of disconnections of such paw from the element 1250 during the measurement interval. Other auxiliary circuits of the device, common to all channels 1000-1 up to 1000-N, as shown in FIG. 3, are a timer 2000 for setting the measurement interval, a sampling generator 3000, feeding sources 5000 and an auxiliary electrical checking circuit 4000 for detecting contamination of the detecting element 1250 by excrements of the laboratory animal. The output changes of state of the detection element 1250 controls the corresponding state of the comparator 1100, which in turn is coupled to the inputs of the circuits 1210, 1230 and 1240.

The conductive adaptation of the test paw of the animal may be accomplished by placing a highly electroconductive and adhesive layer all over the plantar surface of the test paw. The layer may conventionally be formed from a conductive varnish that is quick-drying and non-irritating to the animal's skin.

Figure 2:
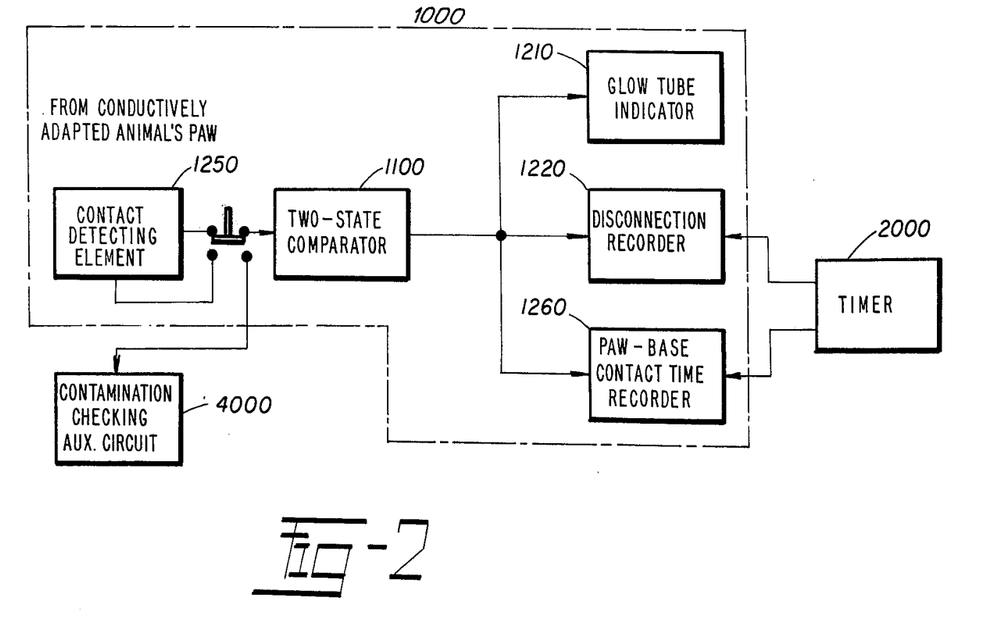
FIG. 2 is a block diagram of one channel of the second described embodiment of the device of the invention provided with means for continuously recording the total time, during a measurement interval, in which a conductively adapted paw of a test animal is in contact with the base.

The detecting element 1250 of FIGS. 1 and 2 may constitute substantially the entire floor of the cage on which the animal stands, and may advantageously be formed from a planar arrangement of parallel metal rods. The rods may illustratively be made from stainless steel 1.5 mm in diameter; and when the test animal is a rat or guinea pig, adjacent rods of the array may be spaced 3-5 mm apart so that the animal's paw will normally contact at least an adjacent pair of the conductors.

Alternate ones of the rods are electrically connected to a first bus bar, while the remaining rods are connected to a second bus bar, the resulting two systems of conductors being normally electrically isolated from one another by an air dielectric. In a typical case, the resulting system of rods may be mounted in a rectangular frame which in turn may be supported inside a rectangular cage to form a base upon which the animal stands. Preferably, such base may be located above a removable bottom of the cage, from which accumulated excrements of the animal may be removed.

Figure 4:
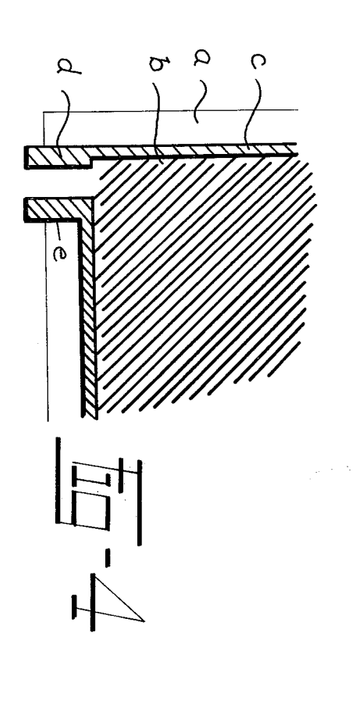
FIG. 4 is a fragmentary detail drawing of one embodiment of a contact detecting element of the device of the invention.

An alternative, solid-dielectric embodiment of the detecting element 1250 of FIGS. 1 and 2 is exemplified in FIG. 4. In this embodiment, the detecting element 1250 is defined on a printed circuit board $a$ formed from an insulating material such as synthetic resin. A plurality of grooves $b$ are photochemically etched in the plate $a$, and a plurality of electroconductive strips of copper foil $c$ are formed intermediate the grooves $b$ in such a way that the adjacent strips are insulated from each other. The output of the element 1250 is formed from a pair of mutually insulated bus bars $d$ and $e$; as indicated, alternate ones of the strips $c$ are connected to the bus bar $d$, while the remaining strips are connected to the bus bar $e$.

The bus bars $d$ and $e$ are disposed at right angles to each other, and illustratively form adjacent legs of a rectangle. The strips $c$ are disposed diagonally to the bus bars as shown.

The oblique disposition of the conductive strips shown in FIG. 4 may also be used with advantage when the element 1250 is in the form of air-spaced metallic rods. Tests have shown that a 45° angle of obliqueness is most advantageous.

Unlike the open-bar arrangement, the solid-dielectric form of element 1250 shown in FIG. 4 is susceptible to contamination by accumulated excrements of the test animal. To prevent such contamination on the element 1250 from affecting the test measurement, a Wheatstone bridge (FIG. 3) of the comparator 1100, to which the output of the element 1250 is applied, is provided in its reference branch with three selective values of resistance, e.g., the resistances 1104, 1105 and 1106. The provision of facilities for switching between such resistances is based on experimental data indicating that the contamination of the element 1250 with urine, for example, is more probably in the case of a larger animal than in the case of a smaller animal. In general, tests have demonstrated that the conductivity of the circuit between the bus bars $d$ and $e$ of FIG. 4 which is produced by the contact of the conductively adapted paw of the animal with the element 1250 falls within the range of 2 ms – 30 s. By contrast, the maximum conductivity of the element 1250 of FIG. 4 which could be produced by a maximum concentration thereon of a small animal's urine, is only 0.5 ms. Thus, the value of the resistance 1105, for example, is chosen to prevent a switching of the output state of the comparator 1100 when the conductivity of the circuit connecting the bus bars during paw-base contact is lower than 2 ms, for example.

In the same manner, the values of the reference branch resistances are chosen to prevent inadvertent operation of the comparator 1100 in the presence of even substantial moisture on the three remaining paws of the animal, which are not conductively adapted but are in continuous contact with the conductors of the element 1250.

A necessary condition for the proper function of the detecting element 1250 is that the current passing through the electroconductive layer of the plantar surface of the test paw should not irritate either the test paw or the other paws of the animal. To meet this requirement, the current passing through the element 1250 should be adjusted to a value not exceeding 70 microamps.

In the recording circuit 1230, the gate 1230-1 consists of a TTL integrated logic circuit 1234 to one input of which there is supplied the output value from the comparator 1100; the amplitude of the mentioned output value is adapted by the transistor 1232. A sampling impulse with a repeating frequency 10 Hz, impulse width 20 usec, is supplied to the second input of the gate 1239. As the polarity change of the input impulse may be both before the sampling impulse and after it, the error is the same on both sides of the Gauss curve according to the Gauss probability rule. With respect to the symmetry of normal rule, the deviation will equal zero. The result of it is that one will get by sampling a real data of the time interval during which the conductively adapted planter surface of the paw is in touch with the detecting element 1250.

Figure 5:
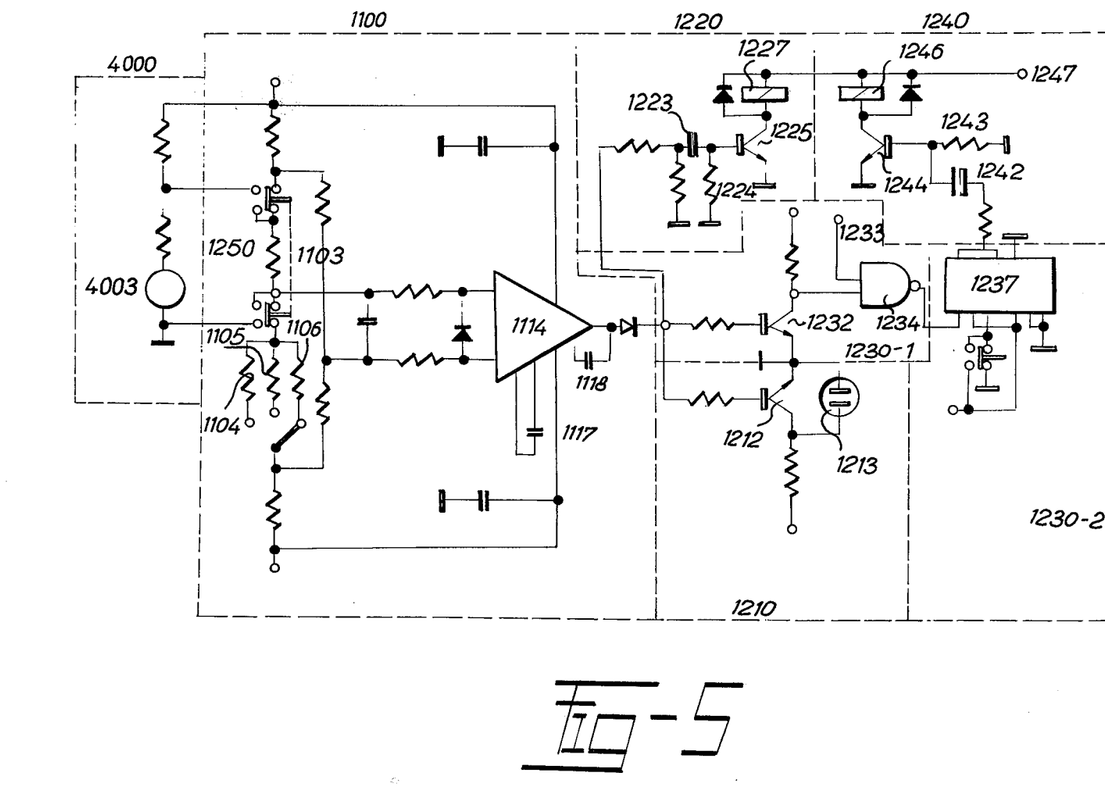
FIG. 5 is a detail wiring diagram of one channel of the first described embodiment of the device of the invention.

The gate 1230-1 with the divider 1230-2 divides the output signal of the gate 1230-1 by ten so that the counting relay in the circuit for a time recording 1240 may indicate total time in seconds. The divider 1230-2 consists of a TTL logic integrated circuit 1237 which is connected as a symmetric divider by ten, which is shown in FIG. 5. A zero setting of all dividers by ten is carried out simultaneously by connecting $Ro_{(2)}$ to the value of log. 1. So the counting relay 1246 records each tenth impulse which is supplied to the input of the divider 1230-2. That is why the recorded time of the whole interval of the paw touch with the base may be a maximum of 0.9 sec. shorter than the real time. This greatest possible error is negligible in comparison to the whole measuring time. The circuit for the time recording 1240 is the circuit that makes possible a summary of time during which the paw conductively adapted was in touch with the detecting element 1250. This circuit consists of a transistor 1244, connected in the switching regime, the collector of which is provided with the counting relay 1246. A filtering RC circuit 1242 and 1243 with a time constant $t = 0.1$ sec. is connected to the base of the transistor. This time constant limits the thermal overheating of the counting relay 1246. The interval of the time recording is limited by a time switching circuit 2000 which disconnects the feeding means 1247 of the switching transistor 1244.

The recording of impulses 1220 is carried out by a circuit for the evaluating of the total number of impulses created by interrupting the paw touch with the detecting element 1250, i.e., the total number of disconnections of the conductively adapted paw from the element 1250 during the measuring interval. This circuit consists of a transistor 1225 connected in a switching system of FIG. 5. Random movements of the animal in the cage will yield, at most, short-duration impulses which are filtered by the R-C element 1223, 1224. The impulse counter 1227 (e.g., a counting relay) works in the same way as the circuit 1240 for time recording during an interval limited by the timer 2000 of FIGS. 1 and 7. The glow tube indicator 1210 permits a visual inspection of the output level of the comparator 1100 which depends upon the resulting resistance of the element 1250 and upon the setting up of the resistance limit value. If this output resistance is lower than the set-up limit value, a glow tube 1213 lights. It occurs in cases, in which the paw of the experimental animal, conductively adapted, is in touch with the element 1250. After the animal was taken out of the measuring box, the glow tube 1213 stops being lighted. To indicate it, one applies a glow tube 1213 parallelly connected to a transistor 1212, which is connected in a switching means. This indication circuit is connected even in the case when the recording circuits are switched off. Auxiliary circuits consist of an circuit 4000 of the sampling generator 3000, of the switching circuit 2000 and of feeding sources 5000.

The circuit 4000 is applied to check the degree of contamination of the element 1250. The scale of the measuring instrument proper 4003 is a non-linear one that one may read the resistance values in a large range with a maximum resolution sensitivity from 0 to 10 kO. The circuit 4000 works under conditions of the same values of voltage and current on the element 1250 which are applied for the proper measuring of the watched quantities. These electrical values eleminate a rise of an electrolytic dissociation at measuring the resistance of the contact plates contaminated by urine. It is necessary to complete this condition, because at a rise of an electrolytic dissociation one gets values misrepresented over a large range. The circuit 4000 is connected, as it is seen in FIGS. 5 and 1, to individual channels by pressing down a push-button 1103; so that simultaneously the switching circuit of the respective channel is disconnected.

Figure 6:
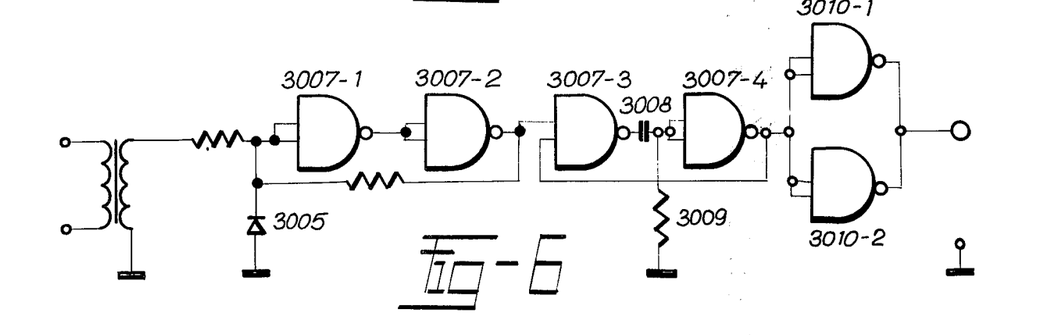
FIG. 6 is a wiring diagram of a sampling generator employed in the first embodiment of the device of the invention.

The sampling generator 3000 quantizes the continuous time intervals, during the measuring duration, over which the conductively adapted test paw is in contact with the element 1250 as shown in FIG. 6, the generator 3000 of sampling impulses consists of a circuit which adapts the mains frequency to a frequency 10 Hz of a rectangular curve. This circuit consists of TTL integrated logic circuits 3007-1 to 3007-4. The input mains frequency is supplied to a simple Schmitt's flip-flop, consisting of gates 3007-1 and 3007-2, where both edges of the impulses are corrected. A diode 3005 protects the input against the influence of negative voltage. The impulse adapted in this way is supplied to a monostable flip-flop, where by means of a feed-back from the output of the gate 3007-4 in the input of the gate 3007-3, the gate 3007-3 is locked during the whole interval $t =$ RC to 3008 and 3009, in which the level log O is in the output. This time constant RC is chosen so that the impulse width may be many times narrower than the shortest possible interruption interval of the contact excited either by a movement or by an insufficient contact of the paw conductively adapted and of the element 1250. In an opposite case, i.e. that the sampling impulse would be wider than the impulse coming from the comparator 1100, then the sampling impulse will be divided into two or more parts in the gate 1230-1, and so the recorded summary time quantity will be increased. The interval of these short impulses, according to the results of our measurements, is approximately greater than or equal to 10 msec. The time constant has been chosen, because of this reason, so that the width of the sampling impulse may be 20 usec.

As the input impulse of this monostable flip-flop is longer than the output impulse, the steepness of the rear edge of the output impulse is decreased, because the gate 3007-3 is locked by the input and the accelerating effect of the feedback cannot take place. That is why it is necessary to improve the steepness of the rear edge of the output impulse by connecting another gate in series, as the gate near the transfer voltage gate gets a high voltage gain, i.e. a big change of an output voltage corresponds to a small change of an input voltage. Because of this fact, the edge of the output signal is steeper than the edge of the input signal. As the output of the generator is connected to more circuits, it was necessary to increase its logic gain by a parallel connection of gates 3010-1 and 3010-2.

The purpose of the timer, shown in FIG. 7, is to limit the total interval of the time recording during which one carries out the measuring of the observed values. The basic frequency which controls the switching circuit is supplied from the sampling generator 3000 having the frequency $f = 10$ Hz. The switching circuit consists of a TTL logic integrated circuit 2005 to 2012. When dividing the frequency 10 Hz by the above-mentioned circuits, one gets intervals 48 sec., 1 minute, 5 minutes, 10 minutes, 15 and 20 minutes that comply with the desired measuring intervals for experiments. One may also select other intervals by means of a manual change-over switch 3015. The proper switching circuit consists of a transistor 2020 connected in a switching means, the collector of which is provided by a relay 2021. If a positive voltage is fed across the base of the transistor by pressing down the push-button 2029, the transistor 2020 switches on and simultaneously it holds down the contact of the relay 2028, and so it holds the transistor 2020 in a switched position until an output signal is supplied from one of the preselected dividers. The terminating derived edge of this signal closes the transistor 2020 and so the hold-on contact of the relay 2028 is released. The other couple of contacts of the relay 2027 is utilized for the connection and disconnection of the feeding voltage of the circuit of the impulses recording and the time circuit. By pressing down a push-button 2029 one sets the transistor 2020 in the closed condition and simultaneously one carries out a zero-setting of all dividers. An advantage of this time switching circuit is its accuracy and reliable operation. Known wirings of time switching circuits with the RC constant do not comply with desired conditions because of their inaccuracy at intervals near 15 minutes, where a thermal dependence of components and a low stability of capacitors affects the results. Known electric switching clocks are not very accurate for these requirements within the desired time range. The source part consists of sources for feeding the operational amplifier of the TTL logic integrated circuits, glow tubes and counting relays.

In FIG. 2 there is shown a variant of a device for measuring nociceptive reactions of laboratory animals, where a continuous time recording is applied.

This second variant consists of a detecting element 1250, of an auxiliary circuit 4000, of a comparator 1100, of a glow tube indicator 1210 and of a circuit 1220 for a recording of pulses the function and wiring of which are identical to the wiring of the device with a discrete time recording. The difference, in comparison with the previous example, the block diagram of which is shown in FIG. 1, is that one carries out the continuous time recording 1260 so that the output voltage of the comparator 1100 controls a transistor 1264, the collector of which is provided with a relay 1266. Contacts 1268, 1269 of this relay 1266 are closed or released in dependence to a selective putting down or lifting of the conductively adapted paw of the animal to the element 1250. The relay switches in an electric stop watch where it is possible to record the whole interval during which the paw was in touch with the base. This time may be read in selected intervals which are to be preselected, in the timer 2000.

The differences between both illustrative embodiments are of a technical character only. The advantage of the embodiment with a continuous recording of time values is that the recording of time quantity is simple and that there is a possiblity to carry out a zero-setting of all electric switching clocks. Appreciable noise caused by closing electric relays in electric switching clock is a disadvantage of this variant. That is why a design of a time value recording by means of counting relays has been carried out. The embodiment of the recording means is less noisy, dimensions are smaller and the incidence of trouble is also lower. The time range is many times larger, which makes possible to summarize the time values.

Without in any way limiting the generality of the foregoing description, the following were illustrative test results using a plurality of test rats whose paws were conductively adapted as indicated above and subjected to nociceptive stimulation whose reaction was measured with the above-described facilities.

EXAMPLE 1

Prior to a nociceptive irritation of the paw of a first rat, the total contact time of its conductively adapted paw with the detecting element 1250 was found to be 18 minutes out of a preselected interval of 20 minutes. After a painful nociceptive irritation of the paw was induced by injecting a solution of formalin into the paw, it was found that the total contact time within the same interval was only 1 minute. The test was then repeated with a second rat, into which a 5 mg/kg dose of morphine was injected prior to the painful stimulation. In such second rat, it was found that the paw-base contact time, when the formalin solution was injected into its paw, was increased to 10 minutes out of the 20 minute test interval. The test was again repeated with a third rat, into which a heavier dose of morphine (10 mg/kg) was injected prior to the application of the nociceptive stimulation. In this case, the paw-base contact time following the injection of the formalin was increased to 18 minutes out of the 20 minute test interval.

EXAMPLE 2

During the same series of tests on the three rats indicated in Example 1, the number of paw-base disconnections were measured. Prior to the introduction of the nociceptive stimulation, a total of 180 disconnections were measured, i.e., 10 disconnections for each of the 18 minutes of the time during which the test paw contacted the element 1250 during the test interval. After the formalin was injected into the first rat, the total number of disconnections was 100 over the single minute of paw-base contact. The second rat, injected with 5 mg/kg of morphine and then given a dose of formalin, exhibited a total of 200 disconnections over the 10 minutes of paw-base contact within the 20 minute test interval, i.e., 20 disconnections per minute of contact-time. The third rat, injected with 10 mg/kg of morphine and then subjected to the formalin treatment, exhibited 90 disconnections during the 18 minutes of paw-base contact within the 20 minute test interval, i.e., 5 disconnections per minute of paw-base contact. Thus, while the nociceptive irritation of a rat's paw can result in a ten-fold increase of the number of paw-base disconnections per minute of paw-base contact time, such increase could be partially or even completely suppressed by a proper dose of an analgesic agent.

Although the invention is illustrated and described with reference to a plurality of preferred embodiments thereof, it is to be expressly understood that it is in no way limited to the disclosure of such a plurality of preferred embodiments, but is capable of numerous modifications within the scope of the appended claims.

What is claimed is:

1. In an apparatus for objectively determining a nociceptive reaction of a caged laboratory animal to an irritating stimulus applied to a first paw of the animal, wherein the reaction is manifested by lifting of the first paw from the base of the cage, the improvement wherein substantially the entire floor of the cage is formed from a planar array which comprises, in combination, a plurality of parallel, dielectrically spaced elongated conductors, the spacing between adjacent ones of the conductors being selected to provide contact between the paw and a pair of adjacent conductors except when the paw is lifted from the floor, first and second mutually insulated bus bars, means for connecting alternate ones of the conductors to the first bus bar, and means for connecting the remaining conductors to the second bus bar; wherein an electroconductive layer is applied over the plantar surface of the first paw whereby the contact of the first paw with the floor normally connects the first and second bus bars through a high-conductivity path, the first and second bus bars being disconnected from each other when the first paw is lifted from the floor; and wherein the apparatus further comprises, in combination, two-state comparator means having an output normally in a first state and operable into a second state upon a prescribed change of state at its input, means for coupling the first and second bus bars to the input of the comparator means for operating the comparator means from its first state to its second state when the first and second bus bars are disconnected, the comparator means reverting to its first state when the bus bars are reconnected, and first means operable over a selected first interval and coupled to the output of the comparator means for measuring the total time over which the comparator means output is in its first state over the first interval.

2. Apparatus as defined in claim 1, in which the comparator means further comprises threshold-operated means for inhibiting the operation of the comparator means from its first to its second state when the conductivity of the path across the first and second bus bars is below a predetermined value.

3. Apparatus as defined in claim 1, in which the apparatus further comprises second means operable over the prescribed first interval and coupled to the output of the comparator means for recording the total number of times during said first interval that the comparator means is operated from its first to its second output state.

4. Apparatus as defined in claim 1, in which the first recording means comprises means for periodically sampling the output of the comparator means, and means coupled to the output of the sampling means for counting the number of the resulting samples.

* * * * *